United States Patent
Pace

(10) Patent No.: US 9,084,725 B2
(45) Date of Patent: Jul. 21, 2015

(54) HAIR CONDITIONING COMPOSITION

(75) Inventor: Emilie Pace, Grenoble (FR)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

(21) Appl. No.: 12/920,115

(22) PCT Filed: Mar. 5, 2009

(86) PCT No.: PCT/EP2009/052619
§ 371 (c)(1),
(2), (4) Date: Oct. 18, 2010

(87) PCT Pub. No.: WO2009/112426
PCT Pub. Date: Sep. 17, 2009

(65) Prior Publication Data
US 2011/0020262 A1 Jan. 27, 2011

(30) Foreign Application Priority Data
Mar. 14, 2008 (EP) .................................... 08152786

(51) Int. Cl.
| | | |
|---|---|---|
| A61K 8/72 | (2006.01) | |
| A61Q 5/12 | (2006.01) | |
| A61K 8/06 | (2006.01) | |
| A61K 8/73 | (2006.01) | |
| A61K 8/891 | (2006.01) | |
| A61K 8/892 | (2006.01) | |
| A61K 8/898 | (2006.01) | |
| A61K 8/90 | (2006.01) | |

(52) U.S. Cl.
CPC ............. *A61K 8/068* (2013.01); *A61K 8/731* (2013.01); *A61K 8/891* (2013.01); *A61K 8/892* (2013.01); *A61K 8/898* (2013.01); *A61K 8/90* (2013.01); *A61Q 5/12* (2013.01); *A61K 2800/262* (2013.01)

(58) Field of Classification Search
None
See application file for complete search history.

(56) References Cited

U.S. PATENT DOCUMENTS

| | | | |
|---|---|---|---|
| 5,374,614 A * | 12/1994 | Behan et al. | 512/3 |
| 5,733,536 A | 3/1998 | Hill | 424/70.12 |
| 6,147,038 A | 11/2000 | Halloran | 510/122 |
| 2005/0158266 A1* | 7/2005 | Peffly et al. | 424/70.12 |
| 2005/0169864 A1* | 8/2005 | Derici et al. | 424/70.11 |
| 2006/0293197 A1 | 12/2006 | Uehara et al. | 510/122 |

FOREIGN PATENT DOCUMENTS

| | | |
|---|---|---|
| EP | 0268982 A2 | 6/1988 |
| EP | 0 490 582 | 6/1992 |
| EP | 0 514 934 | 11/1992 |
| EP | 0514934 | 11/1992 |
| EP | 1 652 555 | 5/2006 |
| JP | 57046911 | 3/1982 |
| JP | 2003-212732 | 7/2003 |
| WO | 03/094874 | 11/2003 |
| WO | 2005/039517 | 5/2005 |
| WO | WO2007002564 A1 | 1/2007 |

OTHER PUBLICATIONS

PCT International Search Report in PCT application PCT/EP2009/052619, Oct. 5, 2009.

* cited by examiner

*Primary Examiner* — Susan Tran
*Assistant Examiner* — William Craigo
(74) *Attorney, Agent, or Firm* — Greenberg Traurig, LLP

(57) ABSTRACT

The present invention relates to an aqueous conditioning serum. Despite the prior art there remains the need for improved serum conditioners. Accordingly, the present invention provides a visually clear aqueous conditioning serum for the hair comprising: 50 to 95% wt. water, 0.1 to 8% wt. silicone microemulsion, 5 to 15% wt. copolymer of ethylene glycol and propylene glycol according to one of the following formula: HO(CH2CH2O)x(CH(CH3)CH2O)y(CH2CH2O)z H (I) HO(CH(CH3)CH2O)x(CHCH2O)y(CH2(CH3)CH2O)z H (II) with the mean value of y in the range from 10 to 60 and the values of x and z both in the range from 1 to 150, 0.5 to 1.5% wt. thickener. The composition according to the invention conditions the hair without depositing too much silicone. Accordingly, it reduces the risk of applying too much and leaving the hair feeling lank and greasy.

9 Claims, No Drawings

HAIR CONDITIONING COMPOSITION

The present invention relates to an aqueous conditioning serum.

Despite the prior art there remains the need for improved serum conditioners.

Accordingly, the present invention provides a visually clear aqueous conditioning serum for the hair comprising:

50 to 95% wt. water, 0.1 to 8% wt. silicone microemulsion, 5 to 15% wt. copolymer of ethylene glycol and propylene glycol according to one of the following formulae:

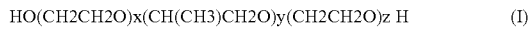

HO(CH2CH2O)x(CH(CH3)CH2O)y(CH2CH2O)z H  (I)

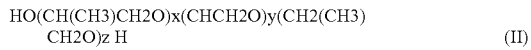

HO(CH(CH3)CH2O)x(CHCH2O)y(CH2(CH3)CH2O)z H  (II)

with the mean value of y in the range from 10 to 60 and the values of x and z both in the range from 1 to 150, 0.5 to 1.5% wt. thickener.

The composition according to the invention conditions the hair without depositing too much silicone. Accordingly, it reduces the risk of applying too much and leaving the hair feeling lank and greasy.

By visually clear is meant that a score of at least +3 is achieved using the following protocol.

The formulation was transferred to a 1 cm path clear cell and placed on a light table above a numeric scale −12 to +10 where the size of the numbers smoothly decrease from 10 mm high (−12) to 0.25 mm low (+10). The clarity of the formulation was given the value to the smallest number that could be read. The figures were placed directly against the light cell.

By silicone microemulsion is meant an emulsion of non-volatile, water-immiscible silicones, either unfunctionalised (i.e. dimethicone/dimethiconol) or functionalised (e.g. amodimethicones, other silicone copolymers) having a mean droplet size below 100 nm, more preferably below 75 nm, most preferably below 50 nm. Such microemulsions can be included in a clear formulation without compromising its clarity.

Suitable silicone emulsions include DC 1870 ex. Dow Corning. Preferably, the composition comprises from 2 to 6% wt. silicone microemulsion. This level of silicone provides the optimum deposition on to the hair without the sensorial negatives associated with too much deposition, e.g. greasy feel and lank hair.

Preferably, the composition comprises from 70 to 80% wt. water. This level of water provides the optimum formulation window for the remaining ingredients.

The copolymer used in the invention confirms to one the following formula:

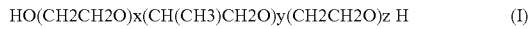

HO(CH2CH2O)x(CH(CH3)CH2O)y(CH2CH2O)z H  (I)

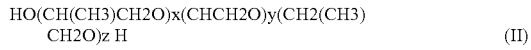

HO(CH(CH3)CH2O)x(CHCH2O)y(CH2(CH3)CH2O)z H  (II)

with the mean value of y in the range from 10 to 60 and the values of x and z both in the range from 1 to 150, Preferably, x & z are less than 10, more preferably less than 5, most preferably less than 2.

Preferably, y is less than 80, more preferably less than 50, even more preferably less than 25, most preferably less than 20.

Preferably, x/y is less than 0.15, more preferably less than 0.1, most preferably less than 0.075.

Preferably, the composition comprises from 8 to 12% wt. copolymer. This provides the optimum foam depression while maintaining clarity of the composition.

The composition may also comprise a copolymer of formula (I) in combination along with a copolymer from formula (II).

Preferably, the polymer is present at from 1 to 20% wt., more preferably at from 5 to 15% wt. and most preferably from 7 to 13% wt. These levels provide the best clarity maintenance.

Preferably, the composition comprises from 0.8 to 1.2% wt. thickener. This provides the optimum rheological properties of the composition. Suitable thickeners include the modified celluloses for example hydroxyethyl cellulose.

Preferably, the composition comprises perfume.

Preferably, the composition comprises a co-solvent for the perfume. Co-solvents prevent light scattering particles forming in the composition and so maintain the clarity of the composition. Preferred co-solvents include alcohols, especially ethanol.

Preferably, the composition comprises a co-surfactant for the perfume. Co-surfactants also prevent light scattering particle formulation and so maintain the clarity of the composition. Preferred co-surfactants include cremophore and also Eumulgin HPS which is composed of Coceth-7 and PPG-1-PEG-9 Lauryl Glycol Ether and PEG-40 Hydrogenated Castor Oil.

Preferably, such co-surfactants are included at from 0.1 to 3% wt. preferably from 1-1.5% wt.

Preferably, the composition comprises a cationic surfactant. Cationic surfactants provide a conditioning benefit to the hair.

Preferably, the composition comprises a fatty material selected from fatty alcohols, fatty acids, fatty amides and fatty esters. Fatty materials provide a conditioning benefit to the hair.

Compositions according to the invention may also comprise any of the known ingredients used in conditioning serums which do not adversely affect the overall clarity of the composition. Typical of such ingredients are water-miscible silicones such as certain aminosilicones or silicone polyethers.

The composition according to the invention may be packaged in any suitable package, for example a spray, compact, squeezy bottle, etc.

EXAMPLE

The following is a composition according to the invention.

It is made by adding half of the water to the Natrosol. Leave it to stir at 153 rpm for 30-40 minutes until solution becomes thick and clear.

Add Glycerol, DMC 6031, and CTAC to the main mix.

Add DC1870 slowly to the main mix.

Add L31, Glydant plus to the main mix and leave it to stir for 10 minutes (the solution should be transparent).

In another beaker, add ethanol, Eumulgin HPS and perfume, stir for 3 minutes and add it to the main mix.

| Ingredient | % wt. active |
| --- | --- |
| Water | 79.85 |
| Hydroxyethylecellulose | 0.85 |
| Glycerin | 3.0 |
| PEG/PPG-25/25 dimethicone DMC6031 | 1.0 |
| Cetyl trimmonium chloride | 0.33 |
| Silicone microemulsion DC 1870 | 3.5 |
| Pluronic L31 | 10.0 |
| DMDM Hydantoin | 0.17 |

-continued

| Ingredient | % wt. active |
|---|---|
| Perfume | 0.1 |
| Eumulgin HPS | 1.2 |
| | 100 |

The invention claimed is:

1. Aqueous conditioning serum for the hair comprising:
50 to 95% wt. water,
0.1 to 8% wt. silicone microemulsion,
8 to 12% wt. copolymer of ethylene glycol and propylene glycol according to one of the following formulae:

   (I)

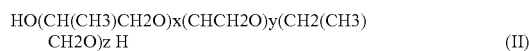   (II)

with the mean value of y in the range from 10 to 60 and the values of x and z both in the range from 1 to 150 and,
0.5 to 1.5% wt. thickener;
wherein the serum is visually clear based on a score of at least +3 determined as follows:
a portion of the serum is transferred to a 1 cm path clear cell and placed on a light table above a numeric scale −12 to +10 where a size of the numbers smoothly decreases from 10 mm high (−12) to 0.25 mm low (+10), and
wherein the score is a value of the smallest number of the numerical scale that could be read.

2. Composition according to claim 1 comprising from 70 to 80% wt. water.

3. Composition according to claim 1 comprising from 2 to 6% wt. silicone microemulsion.

4. Composition according to claim 1 comprising from 0.8 to 1.2% wt. thickener.

5. Composition according to claim 1 further comprising perfume.

6. Composition according to claim 1 comprising a co-solvent for the perfume.

7. Composition according to claim 1 further comprising a co-surfactant for the perfume.

8. Composition according to claim 1 further comprising a cationic surfactant.

9. Composition according to claim 1 further comprising a fatty material selected from fatty alcohols, fatty acids, fatty amides and fatty esters.

* * * * *